US008808964B2

(12) United States Patent
Sagehashi et al.

(10) Patent No.: US 8,808,964 B2

(45) **Date of Patent: *Aug. 19, 2014**

(54) NITROGEN-CONTAINING ORGANIC COMPOUND, CHEMICALLY AMPLIFIED POSITIVE RESIST COMPOSITION, AND PATTERNING PROCESS

(75) Inventors: Masayoshi Sagehashi, Joetsu (JP); Takeru Watanabe, Joetsu (JP); Tomohiro Kobayashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 23 days.

This patent is subject to a terminal disclaimer.

(21) Appl. No.: 13/217,319

(22) Filed: Aug. 25, 2011

(65) Prior Publication Data

US 2012/0052441 A1 Mar. 1, 2012

(30) Foreign Application Priority Data

Aug. 26, 2010 (JP) ................................ 2010-189289

(51) Int. Cl.
*G03F 7/004* (2006.01)

(52) U.S. Cl.
USPC ....................................... 430/270.1; 430/322

(58) Field of Classification Search
USPC ...................................................... 430/270.1
See application file for complete search history.

(56) References Cited

U.S. PATENT DOCUMENTS

| | | | | |
|---|---|---|---|---|
| 6,187,504 | B1 | 2/2001 | Suwa et al. | |
| 6,322,949 | B2 | 11/2001 | Suwa et al. | |
| 6,566,533 | B1 * | 5/2003 | Barth et al. | 548/441 |
| 7,511,169 | B2 | 3/2009 | Ohsawa et al. | |
| 7,771,914 | B2 | 8/2010 | Hatakeyama et al. | |
| 7,919,226 | B2 | 4/2011 | Ohsawa et al. | |
| 2001/0000259 | A1 * | 4/2001 | Hall-Goulle | 528/117 |
| 2007/0231738 | A1 | 10/2007 | Kaneko et al. | |
| 2009/0081588 | A1 | 3/2009 | Hatakeyama et al. | |
| 2009/0208873 | A1 | 8/2009 | Harada et al. | |
| 2009/0269696 | A1 * | 10/2009 | Ohsawa et al. | 430/270.1 |
| 2009/0274978 | A1 | 11/2009 | Ohashi et al. | |
| 2010/0112482 | A1 | 5/2010 | Watanabe et al. | |
| 2010/0136482 | A1 | 6/2010 | Harada et al. | |
| 2012/0135350 | A1 * | 5/2012 | Kobayashi et al. | 430/285.1 |

FOREIGN PATENT DOCUMENTS

| | | | | |
|---|---|---|---|---|
| JP | 3632410 | B2 | | 3/2005 |
| JP | 2007-145797 | A | | 6/2007 |
| JP | 3995575 | B2 | | 10/2007 |
| JP | 2007-297590 | A | | 11/2007 |
| JP | 2008-122932 | A | | 5/2008 |
| JP | 2008-299069 | A | | 12/2008 |
| JP | 2009-98638 | A | | 5/2009 |
| JP | 2009-191151 | A | | 8/2009 |
| JP | 2009-269953 | A | | 11/2009 |
| JP | 2010-107695 | A | | 5/2010 |
| JP | 2010-134012 | A | | 6/2010 |
| JP | 2012008553 | A | * | 1/2012 |
| JP | 2012113143 | A | * | 6/2012 |
| JP | 2012128198 | A | * | 7/2012 |
| KR | 10-0556646 | B1 | | 3/2006 |
| KR | 10-2006-0107340 | A | | 10/2006 |
| KR | 10-2009-0115678 | A | | 11/2009 |

OTHER PUBLICATIONS

Dammel et al., "193 nm Immersion Lithography—Taking the Plunge," Journal of Photopolymer Science and Technology, 2004, vol. 17, No. 4, p. 587-601.
File Registry on STN, 202523-18-0/RN, Entered STN: Mar. 12, 1998.
File Registry on STN, 202523-26-0/RN, Entered STN: Mar. 12, 1998.
File Registry on STN, 202523-30-6/RN, Entered STN: Mar. 12, 1998.
File Registry on STN, 22129-07-3/RN, Entered STN: Nov. 16, 1984.
File Registry on STN, 392232-64-3/RN, Entered STN: Feb. 14, 2002.
File Registry on STN, 492998-44-4/RN, Entered STN: Feb. 21, 2003.
File Registry on STN, 74061-49-7/RN, Entered STN: Nov. 16, 1984.

* cited by examiner

*Primary Examiner* — Cynthia H Kelly
*Assistant Examiner* — Anna Malloy
(74) *Attorney, Agent, or Firm* — Birch, Stewart, Kolasch & Birch, LLP

(57) ABSTRACT

An aralkylcarbamate of imidazole base is effective as the quencher. In a chemically amplified positive resist composition comprising the carbamate, deprotection reaction of carbamate takes place by reacting with the acid generated upon exposure to high-energy radiation, whereby the composition changes its basicity before and after exposure, resulting in a pattern profile with advantages including high resolution, rectangular shape, and minimized dark-bright difference.

4 Claims, No Drawings

NITROGEN-CONTAINING ORGANIC COMPOUND, CHEMICALLY AMPLIFIED POSITIVE RESIST COMPOSITION, AND PATTERNING PROCESS

CROSS-REFERENCE TO RELATED APPLICATION

This non-provisional application claims priority under 35 U.S.C. §119(a) on Patent Application No. 2010-189289 filed in Japan on Aug. 26, 2010, the entire contents of which are hereby incorporated by reference.

TECHNICAL FIELD

This invention relates to a novel nitrogen-containing organic compound, a chemically amplified positive resist composition comprising the compound, and a patterning process using the composition.

BACKGROUND ART

While a number of recent efforts are being made to achieve a finer pattern rule in the drive for higher integration and operating speeds in LSI devices, DUV and EUV lithography is thought to hold particular promise as the next generation in microfabrication technology. In particular, photolithography using an ArF excimer laser as the light source is thought requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Journal of Photopolymer Science and Technology, Vol. 17, No. 4, p 587 (2004). While the ArF immersion lithography has entered the commercial stage, the technology still needs a resist material which is substantially insoluble in water.

In the ArF lithography (193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Studies have also been made on photoacid generators (PAGs). As the PAG in ArF chemically amplified resist compositions, triphenylsulfonium salts are typically used because of stability in resist (see JP-A 2007-145797). The triphenylsulfonium salts, however, have the drawback that they exhibit substantial absorption at the ArF exposure wavelength (193 nm) to reduce the transmittance of a resist film, sometimes leading to a low resolution and a less rectangular pattern profile. Aiming at a higher sensitivity and resolution, JP 3632410 reports the development of 4-alkoxynaphthyl-1-tetrahydrothiophenium cations and JP 3995575 discloses a resist composition comprising a resin having a plurality of acid labile groups in combination with such salt. The naphthyl-1-tetrahydrothiophenium salt suffers from a low stability in resist solution due to the alkylsulfonium salt structure susceptible to nucleophilic displacement reaction and a substantial difference in line width or pattern profile between grouped and isolated patterns, which are generally referred to as "dark-bright difference." In particular, the pattern profile difference between dark and bright areas is a problem. The dark area is a light-shielded area including a 10 line-and-space pattern flanked with bulk patterns (in the case of positive tone resist), and the bright area is a transmissive area including a 10 line-and-space pattern flanked with broad spaces (in the case of positive tone resist). Although optical conditions at the center of the 10 line-and-space pattern are equal between the dark and bright areas, a pattern profile difference arises between the dark and bright areas.

According to the inventors' research work, the alkylsulfonium salt could be improved in shelf stability in resist compositions by converting the primary or secondary amine to a t-butoxycarbonyl carbamate, that is, a less nucleophilic nitrogen-containing organic compound. There is still left a room to address the dark-bright difference.

CITATION LIST

Patent Document 1: JP-A 2007-145797 (U.S. Pat. Nos. 7,511,169, 7,919,226, KR 20060107340)

Patent Document 2: JP 3632410 (U.S. Pat. Nos. 6,187,504, 6,322,949, KR 100556646)

Patent Document 3: JP 3995575

Non-Patent Document 1: Journal of Photopolymer Science and Technology, Vol. 17, No. 4, p 587 (2004)

SUMMARY OF INVENTION

An object of the invention is to provide a nitrogen-containing organic compound which is used as a quencher to formulate a resist composition; a resist composition comprising the nitrogen-containing organic compound which exhibits an improved resolution and forms a pattern of rectangular profile and minimized dark-bright difference when processed by photolithography using high-energy radiation, typically ArF excimer laser or EUV; and a pattern forming process using the composition.

The inventors have found that a resist composition comprising a nitrogen-containing organic compound having the general formula (1) below as the quencher offers advantages including resolution, rectangular pattern profile, and shelf stability of alkylsulfonium salts, and is suited for high accuracy micropatterning.

In one aspect, the invention provides a nitrogen-containing organic compound having the general formula (1).

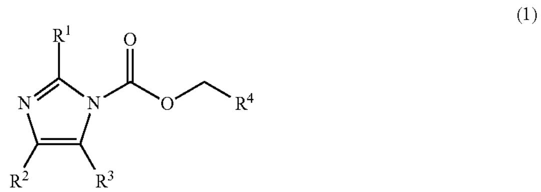

(1)

Herein $R^1$ is hydrogen, a straight, branched or cyclic alkyl group, or $C_6$-$C_{15}$ aryl group, $R^2$ and $R^3$ are each independently hydrogen, a straight, branched or cyclic $C_1$-$C_{10}$ alkyl group, or $C_6$-$C_{15}$ aryl group, $R^2$ and $R^3$ may bond together to form a ring with the carbon atoms to which they are attached, and $R^4$ is an optionally alkoxy-substituted $C_6$-$C_{15}$ aryl group.

In another aspect, the invention provides a chemically amplified positive resist composition comprising the nitrogen-containing organic compound defined above as a quencher. In a preferred embodiment, the chemically amplified positive resist composition comprises (A) the nitrogen-containing organic compound defined above as a quencher, (B) an organic solvent, (C) a base resin which changes its solubility in alkaline developer under the action of an acid, and (D) a photoacid generator.

More preferably, the photoacid generator (D) is a sulfonium salt having the general formula (2):

(2)

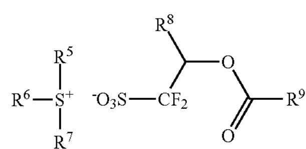

wherein $R^5$, $R^6$, and $R^7$ are each independently a straight or branched alkyl, alkenyl or oxoalkenyl group of 1 to 10 carbon atoms which may contain fluorine, hydroxyl or ether bond, or a substituted or unsubstituted aryl, aralkyl or aryloxoalkyl group of 6 to 18 carbon atoms, or two or more of $R^5$, $R^6$, and $R^7$ may bond together to form a ring with the sulfur atom to which they are attached, $R^8$ is hydrogen or trifluoromethyl, and $R^9$ is a monovalent, straight, branched or cyclic $C_6$-$C_{30}$ hydrocarbon group which may contain a heteroatom.

In a further aspect, the invention provides a process for forming a pattern, comprising the steps of coating the resist composition defined above onto a substrate, heat treating the composition to form a resist film, exposing the resist film to high-energy radiation through a photomask, optionally heat treating, and developing the exposed resist film with a developer; or a process for forming a pattern, comprising the steps of coating the resist composition defined above onto a substrate, heat treating the composition to form a resist film, coating a protective film onto the resist film, exposing the resist film to high-energy radiation through a photomask with water held between the substrate and a projection lens, optionally heat treating, and developing the exposed resist film with a developer.

ADVANTAGEOUS EFFECTS OF INVENTION

The nitrogen-containing organic compound of the invention is a carbamate, especially aralkylcarbamate of an imidazole base. In the chemically amplified positive resist composition comprising the nitrogen-containing organic compound, deprotection reaction of carbamate takes place by reacting with the acid generated upon exposure to high-energy radiation, whereby the composition changes its basicity before and after exposure. This results in a favorable resist pattern with advantages including high resolution, rectangular profile, and minimized dark-bright difference. In addition, the compound is effective for rendering the alkylsulfonium salt shelf stable. The compound is quite useful as the quencher in the chemically amplified positive resist composition.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. The acronym "PAG" stands for photoacid generator.

N-Containing Compound

In search for a compound which offers a high resolution and a better pattern profile when formulated in a chemically amplified positive resist composition, the inventors have found that a nitrogen-containing organic compound having the general formula (1) can be readily prepared in high yields by the method to be described later, that the compound can be used to formulate a chemically amplified positive resist composition capable of forming a pattern with advantages including a high resolution, rectangular profile, and minimized dark-bright difference, and that the compound is effective for rendering alkylsulfonium salts shelf stable.

(1)

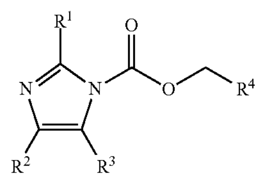

Herein $R^1$ is hydrogen, a straight, branched or cyclic $C_1$-$C_{15}$ alkyl group, or a $C_6$-$C_{15}$ aryl group, $R^2$ and $R^3$ are each independently hydrogen, a straight, branched or cyclic $C_1$-$C_{10}$ alkyl group, or a $C_6$-$C_{15}$ aryl group, $R^2$ and $R^3$ may bond together to form a ring with the carbon atoms to which they are attached, and $R^4$ is an optionally alkoxy-substituted $C_6$-$C_{15}$ aryl group.

Examples of the straight, branched or cyclic $C_1$-$C_{15}$ alkyl group and $C_6$-$C_{15}$ aryl group represented by $R^1$ include, but are not limited to, methyl, ethyl, propyl, isopropyl, undecanyl, and phenyl.

Examples of the straight, branched or cyclic $C_1$-$C_{10}$ alkyl group and $C_6$-$C_{15}$ aryl group represented by $R^2$ and $R^3$ include, but are not limited to, methyl and phenyl.

When $R^2$ and $R^3$, taken together, form a ring, structures having the general formula (3) are exemplary of the ring.

(3)

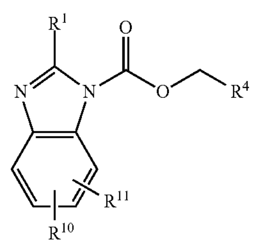

Herein $R^1$ and $R^4$ are as defined above, $R^{10}$ and $R^{11}$ are each independently hydrogen or $C_1$-$C_6$ alkyl.

Examples of the optionally alkoxy-substituted $C_6$-$C_{15}$ aryl group represented by $R^4$ include, but are not limited to, phenyl and 4-methoxyphenyl.

Illustrative, non-limiting examples of the compound having formula (1) are given below.
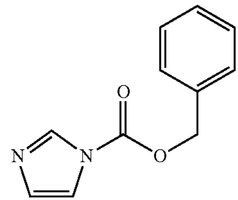
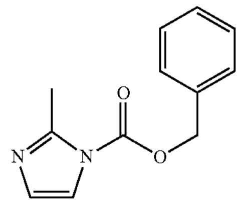
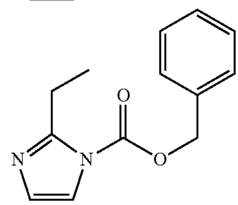
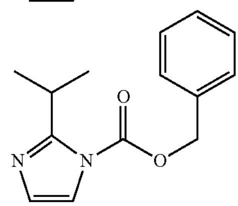
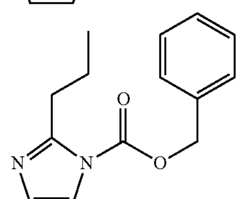
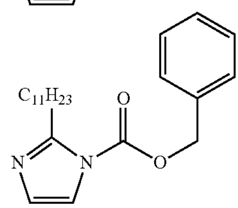
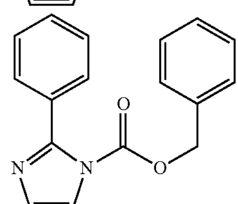
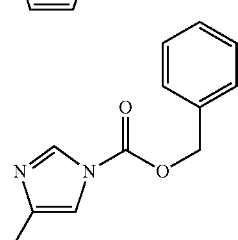
-continued
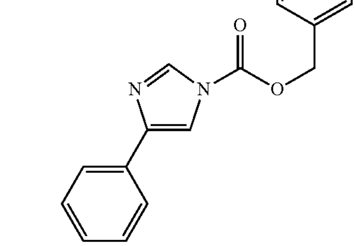
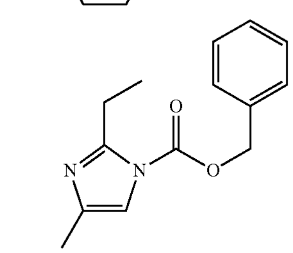
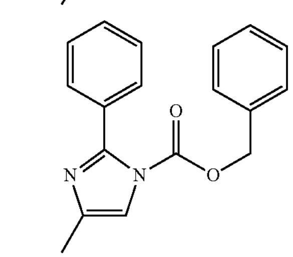
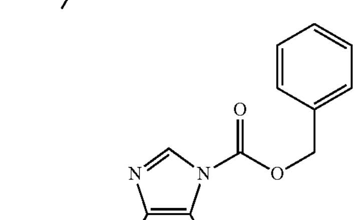
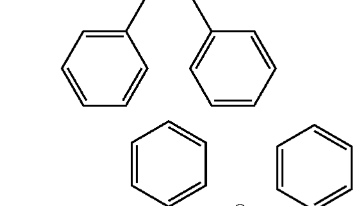
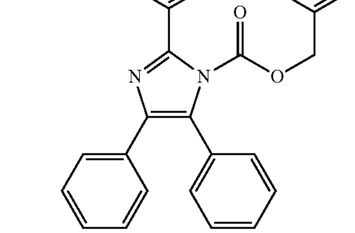
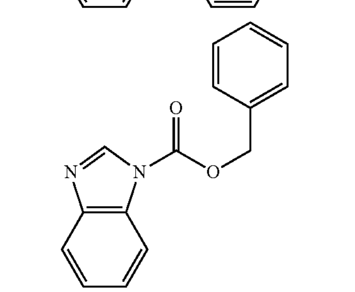

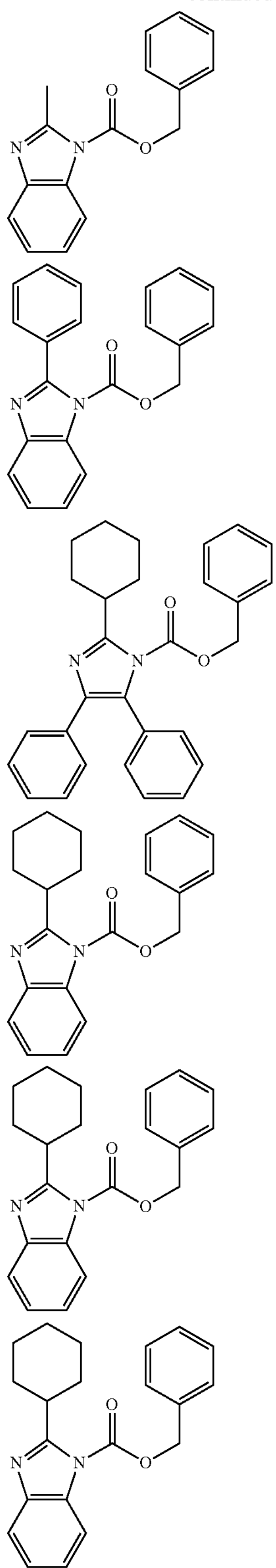
O
N
N
O
O
N
N
O
O
N
N
O
O
N
N
O
O
N
N
O
O
N
N
O
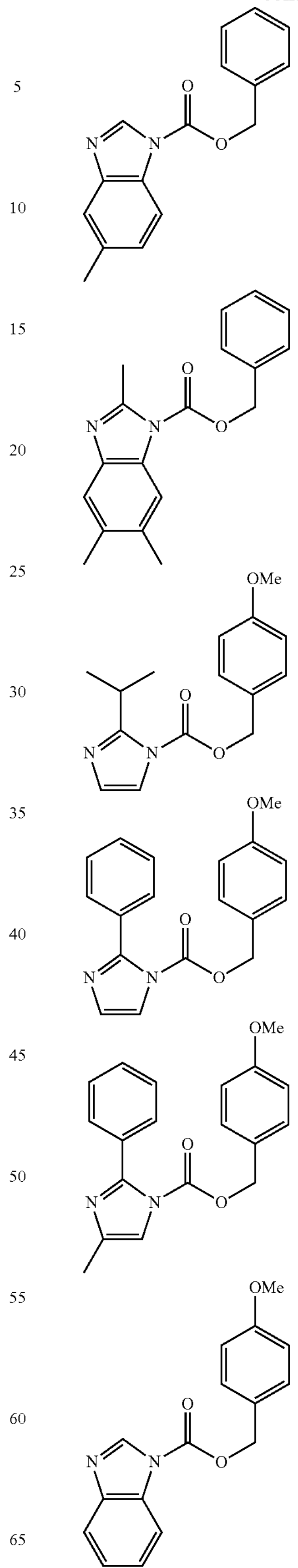
O
N
N
O
O
N
N
O
OMe
O
N
N
O
OMe
O
N
N
O
OMe
O
N
N
O
OMe
O
N
N
O -continued

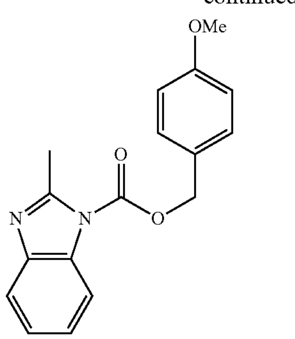

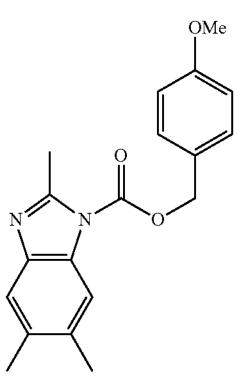

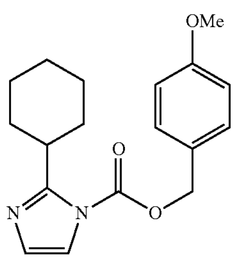

-continued

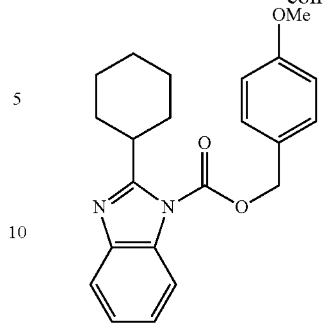

Herein Me stands for methyl.

The nitrogen-containing organic compound having formula (1) may be prepared by the following reaction scheme, for example, although the method is not limited thereto.

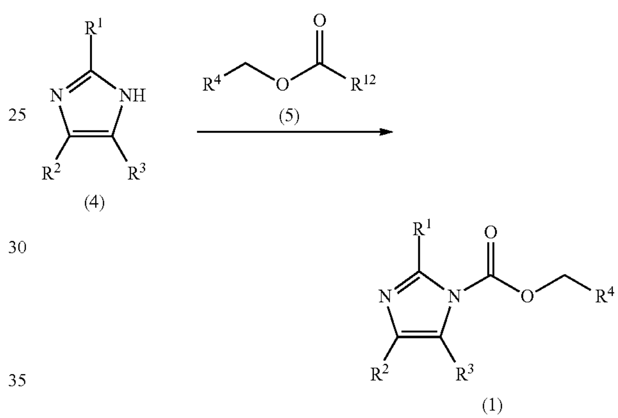

Herein $R^1$ to $R^4$ are as defined above, and $R^{12}$ is halogen or —$OR^{13}$, wherein $R^{13}$ is a group having the following formula (6):

(6)

wherein the broken line designates a valence bond and $R^4$ is as defined above.

In general, the carbamate-forming reaction using imidazole derivative (4) and arylmethoxycarbonyl reagent (5) according to the above scheme is applicable to the synthesis of all compounds having formula (1).

The arylmethoxycarbonyl reagent (5) is preferably a halo-carbonate ester (specifically formula (5) wherein $R^{12}$ is halogen) or a dicarbonate diester (specifically formula (5) wherein $R^{12}$ is —$OR^{13}$). When a halo-carbonate ester is used as reagent (5), the reaction may be conducted in a solventless system or in a solvent such as methylene chloride, acetonitrile, diethyl ether, tetrahydrofuran, N,N-dimethylformamide, toluene, or hexane, by sequentially or simultaneously adding the imidazole derivative (4), the halo-carbonate ester such as benzyl chlorocarbonate or 4-methoxybenzyl chlorocarbonate, and a base such as triethylamine, pyridine, 2,6-lutidine, or N,N-dimethylaniline, and optionally cooling or heating. When a dicarbonate diester is used as reagent (5), the reaction may be conducted in a solvent such as methylene chloride, acetonitrile, diethyl ether, tetrahydrofuran, N,N-dimethylformamide, toluene, or hexane, by sequentially or simultaneously adding the imidazole derivative (4), the dicarbonate diester such as dibenzyl dicarbonate or di(4-methoxybenzyl)dicarbonate, and a base such as triethylamine, pyridine, 2,6-lutidine, or N,N-dimethylaniline, and optionally cooling or heating. The amount of arylmethoxycarbonyl reagent (5) used varies depending on other conditions, but is desirably 1.0 to 5.0 moles, more desirably 1.0 to 2.0 moles per mole of imidazole derivative (4). The amount of the base used varies depending on other conditions, but is desirably 0 to 5.0 moles, more desirably 0 to 2.0 moles per mole of imidazole derivative (4). The reaction time is preferably determined as appropriate for gaining higher yields by monitoring the progress of reaction by thin-layer chromatography (TLC) or gas chromatography (GC) until the reaction is driven to completion. Usually the reaction time is about 0.5 to about 40 hours. The nitrogen-containing organic compound (I) may be recovered from the reaction mixture by ordinary aqueous work-up. If necessary, the compound may be purified by standard techniques like distillation, recrystallization, and chromatography. Alternatively, the aqueous work-up is omitted, and the reaction solution may be purified directly or after filtering off the salt resulting from reaction.

Resist Composition

In the second aspect, the invention provides a chemically amplified positive resist composition comprising the nitrogen-containing organic compound having formula (1) as a quencher or basic compound. One embodiment is a chemically amplified positive resist composition comprising (A) the nitrogen-containing organic compound having formula (1), (B) an organic solvent, (C) a base resin which changes its solubility in alkaline developer under the action of an acid, and (D) a photoacid generator. Optionally, the positive resist composition may further comprise one or more of the following components: (E) a surfactant, (F) a nitrogen-containing organic compound other than the foregoing nitrogen-containing organic compound, (G) an organic acid derivative and/or fluorinated alcohol, and (H) a dissolution inhibitor having a weight average molecular weight of up to 3,000.

The nitrogen-containing organic compound as component (A) is as defined above. It may preferably be compounded in an amount of 0.001 to 12 parts, more preferably 0.01 to 8 parts by weight per 100 parts by weight of the base resin.

The other components including (B) the organic solvent, (C) the base resin which changes its solubility in alkaline developer under the action of an acid, (D) the PAG, (E) the surfactant, (F) the auxiliary nitrogen-containing organic compound, (G) the organic acid derivative and/or fluorinated alcohol, and (H) the dissolution inhibitor having Mw≤3,000 are described in detail in JP-A 2009-269953 (US 2009274978, KR 20090115678), which is incorporated herein by reference.

The organic solvent (B) used herein may be any organic solvent in which the base resin, PAG, and other components are soluble. Illustrative examples of the organic solvent are described in JP-A 2009-269953. The solvents may be used alone or in combinations of two or more.

Of many examples of the organic solvent (B), it is recommended to use diethylene glycol dimethyl ether, 1-ethoxy-2-propanol, propylene glycol monomethyl ether acetate (PGMEA), cyclohexanone, 4-butyrolactone, and mixtures thereof because the acid generator is most soluble therein.

An appropriate amount of the organic solvent used is 200 to 3,000 parts, especially 400 to 2,500 parts by weight per 100 parts by weight of the base resin.

The base resin as component (C) may be selected from the polymers described in JP-A 2009-269953. The acid labile group in the polymer is preferably selected from those groups of formulae (L3) and (L4) described therein. Polymethacrylate is a typical resin. Such polymers may be added alone or in admixture of two or more. The use of plural polymers allows for easy adjustment of resist properties.

The base resins used herein as component (C) include polyhydroxystyrene (PHS), and copolymers of PHS with styrene, (meth)acrylic acid esters or other polymerizable olefinic compounds, for KrF excimer laser resist use; (meth)acrylic acid ester polymers, alternating copolymers of cycloolefin with maleic anhydride and similar copolymers further containing vinyl ethers or (meth)acrylic acid esters, polynorbornene, cycloolefin ROMP polymers, and hydrogenated cycloolefin ROMP polymers, for ArF excimer laser resist use; and fluorinated forms of the foregoing polymers (for both KrF and ArF laser uses) for $F_2$ excimer laser resist use, although the base resins are not limited to these polymers. The base resins may be used alone or in admixture of two or more. In the case of positive resist compositions, it is a common practice to substitute acid labile groups for hydroxyl groups on phenols, carboxyl groups or fluorinated alkyl alcohols for reducing the rate of dissolution in unexposed regions.

The polymer as base resin (C) may comprise recurring units containing an acid labile group of the general formula (C1) and preferably recurring units of at least one type having the general formulae (C2) to (C4), shown below.

(C1)

(C2)

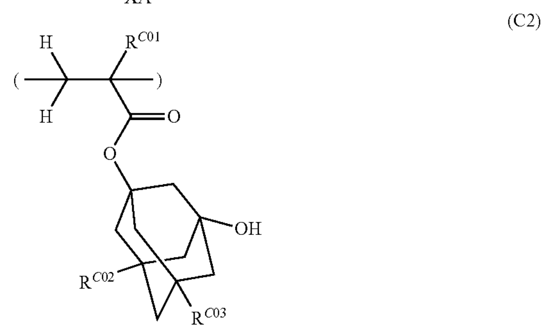

(C3)

(C4)

Herein, $R^{C01}$ is hydrogen, fluorine, methyl or trifluoromethyl, $R^{C02}$ and $R^{C03}$ are each independently hydrogen or hydroxyl, XA is an acid labile group, YL is a lactone structure-containing substituent group, and ZA is hydrogen, $C_1$-$C_{15}$ fluoroalkyl group or $C_1$-$C_{15}$ fluoroalcohol-containing substituent group.

Under the action of an acid, a polymer comprising recurring units of formula (C1) is decomposed to generate a carboxylic acid and turns into an alkali-soluble polymer. The acid labile groups represented by XA may be selected from a variety of such groups, for example, groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

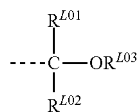

(L2)

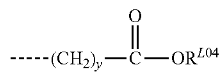

(L3)

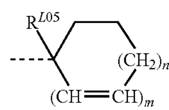

(L4)

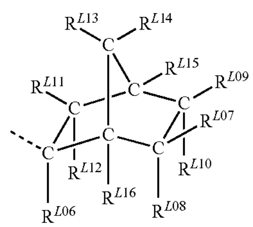

The broken line indicates a valence bond.

In formula (L1), $R^{L01}$ and $R^{C02}$ are hydrogen or straight, branched or cyclic alkyl groups of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached, and in this case, each participant of ring-forming $R^{L01}$, $R^{L02}$ and $R^{L03}$ is a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1); and y is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. The subscript m is 0 or 1, n is 0, 1, 2 or 3, and 2m+n is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. $R^{L07}$ to $R^{L16}$ independently represent hydrogen or monovalent $C_1$-$C_{15}$ hydrocarbon groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). In this case, each group participating in ring formation is a divalent $C_1$-$C_{15}$ hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

The polymer used herein should desirably have a weight average molecular weight (Mw) of 1,000 to 500,000, and desirably 2,000 to 30,000, as determined by gel permeation chromatography (GPC) versus polystyrene standards. A polymer having too low Mw is likely to dissolve in water whereas a polymer having too high Mw can cause a lowering of alkali solubility and defects upon spin coating.

The PAG (D) may be any compound capable of generating an acid upon exposure to high-energy radiation. Suitable PAGs include the sulfonium salts defined and the PAGs described as component (F) in JP-A 2009-269953 and the PAGs described in JP 3995575, and specifically, sulfonium salt, iodonium salt, sulfonyldiazomethane, N-sulfonyloxyimide, and oxime-O-sulfonate acid generators.

Among others, sulfonium salts having the following formula (2) are preferred.

(2)

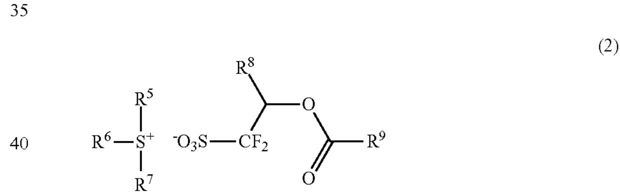

Herein $R^5$, $R^6$, and $R^7$ are each independently a straight or branched alkyl, alkenyl or oxoalkenyl group of 1 to 10 carbon atoms which may contain fluorine, hydroxyl or ether bond, or a substituted or unsubstituted aryl, aralkyl or aryloxoalkyl group of 6 to 18 carbon atoms, or two or more of $R^5$, $R^6$, and $R^7$ may bond together to form a ring with the sulfur atom to which they are attached. $R^8$ is hydrogen or trifluoromethyl. $R^9$ is a monovalent, straight, branched or cyclic $C_6$-$C_{30}$ hydrocarbon group which may contain a heteroatom.

Examples of the sulfonium cation in formula (2) are given below, but not limited thereto.

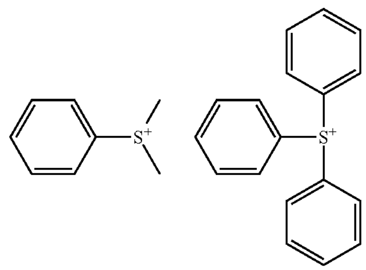

-continued
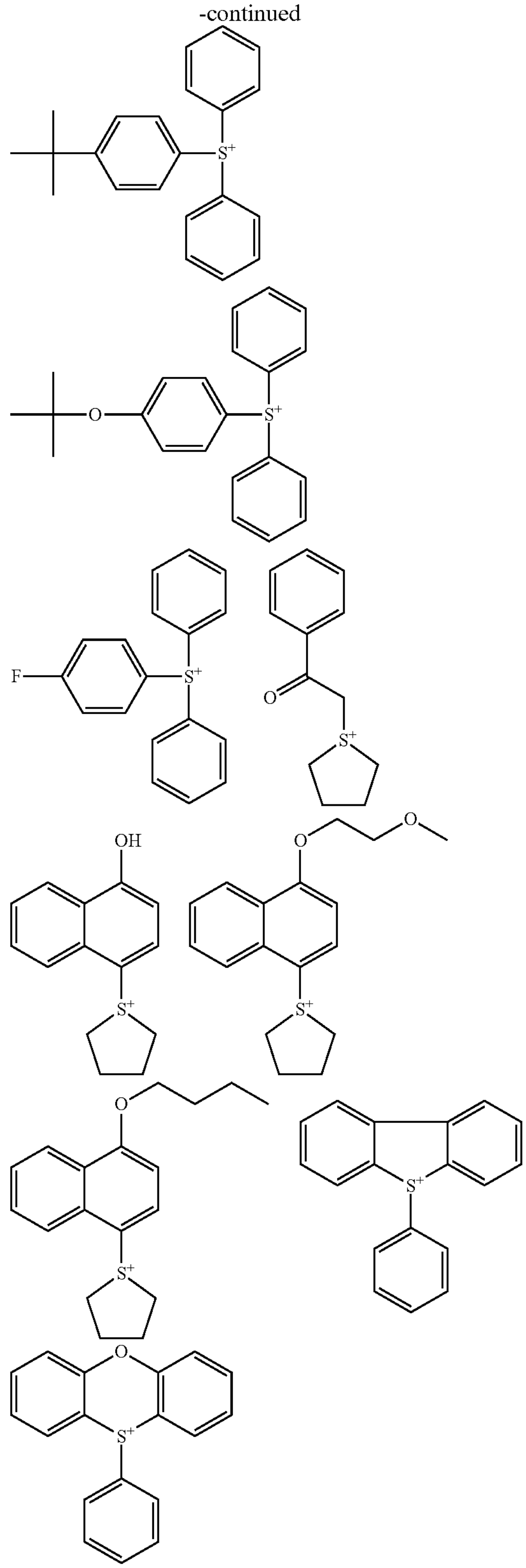
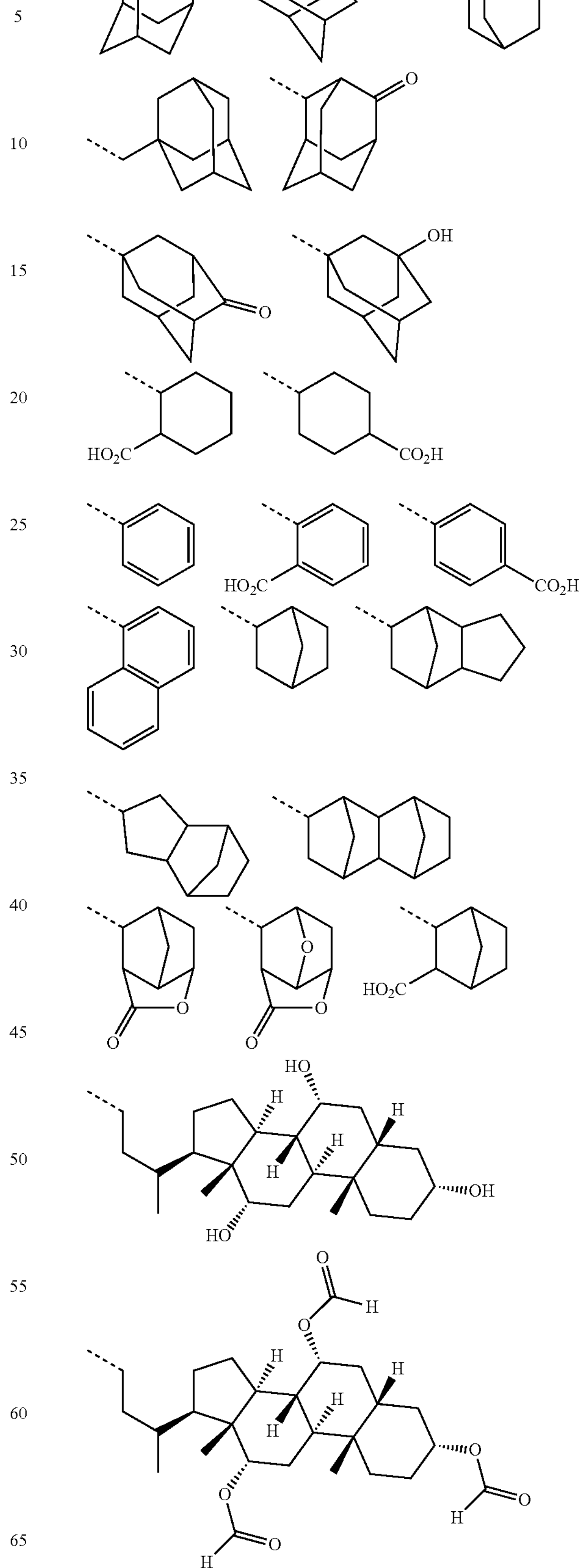
In formula (2), the substituent group $R^8$ on the sulfonate anion is hydrogen or trifluoromethyl. Trifluoromethyl is preferred in view of solubility of the sulfonium salt and resolution.
Examples of the substituent group $R^9$ on the sulfonate anion in formula (2) are given below, but not limited thereto.

-continued

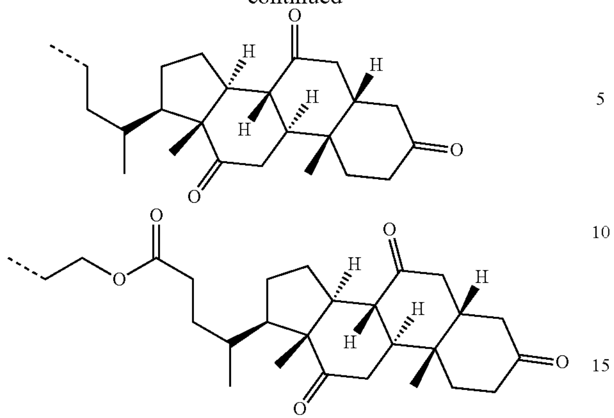

With respect to the sulfonium cation and the sulfonate anion in formula (2), an appropriate combination may be selected by taking into account the stability of sulfonium cation in resist material, acid generation efficiency at the exposure wavelength, and diffusion of acid generated therefrom. Exemplary preferred sulfonium salts are shown below.

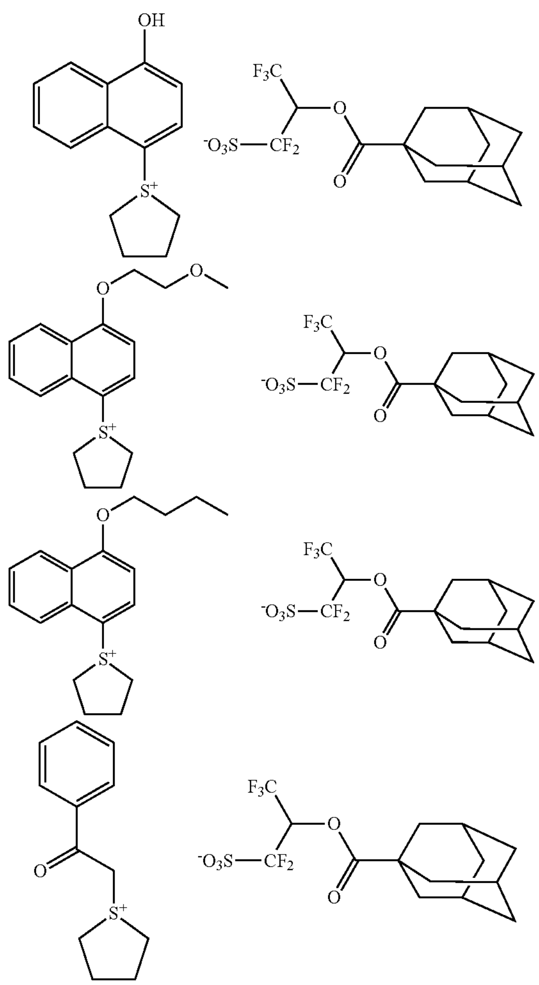

When the alkylsulfonium salt is used in a resist composition along with the nitrogen-containing organic compound defined herein, the composition undergoes no or little sensitivity change during shelf storage and maintains an ability to form a pattern profile at a high resolution.

It is noted that sulfonium salts having the general formulae (1a) and (1b) are novel substances.

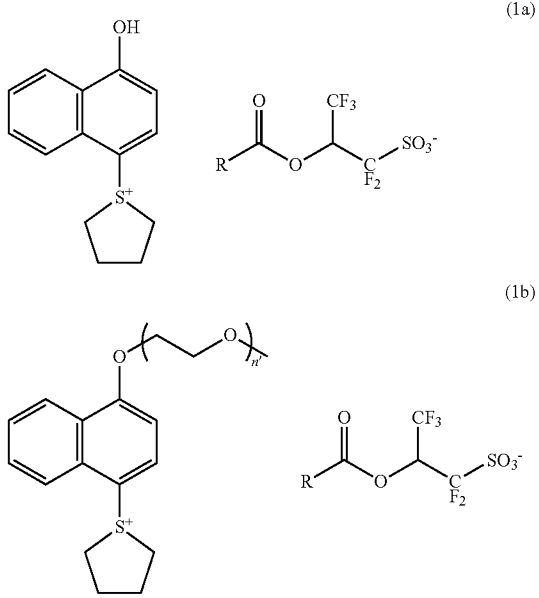

Herein R is a monovalent, straight, branched or cyclic $C_7$-$C_{30}$ hydrocarbon group which may contain a heteroatom, and n' is an integer of 1 to 4, preferably equal to 2, 3 or 4.

Examples of the monovalent, straight, branched or cyclic $C_7$-$C_{30}$ hydrocarbon group which may contain a heteroatom, represented by R, are given below.

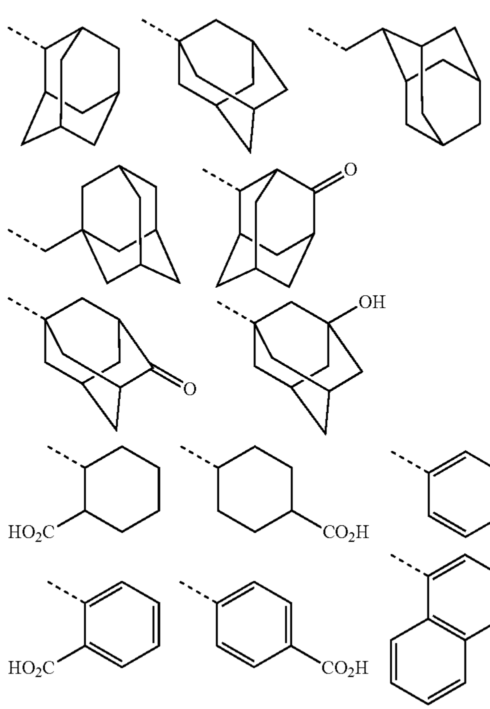

-continued

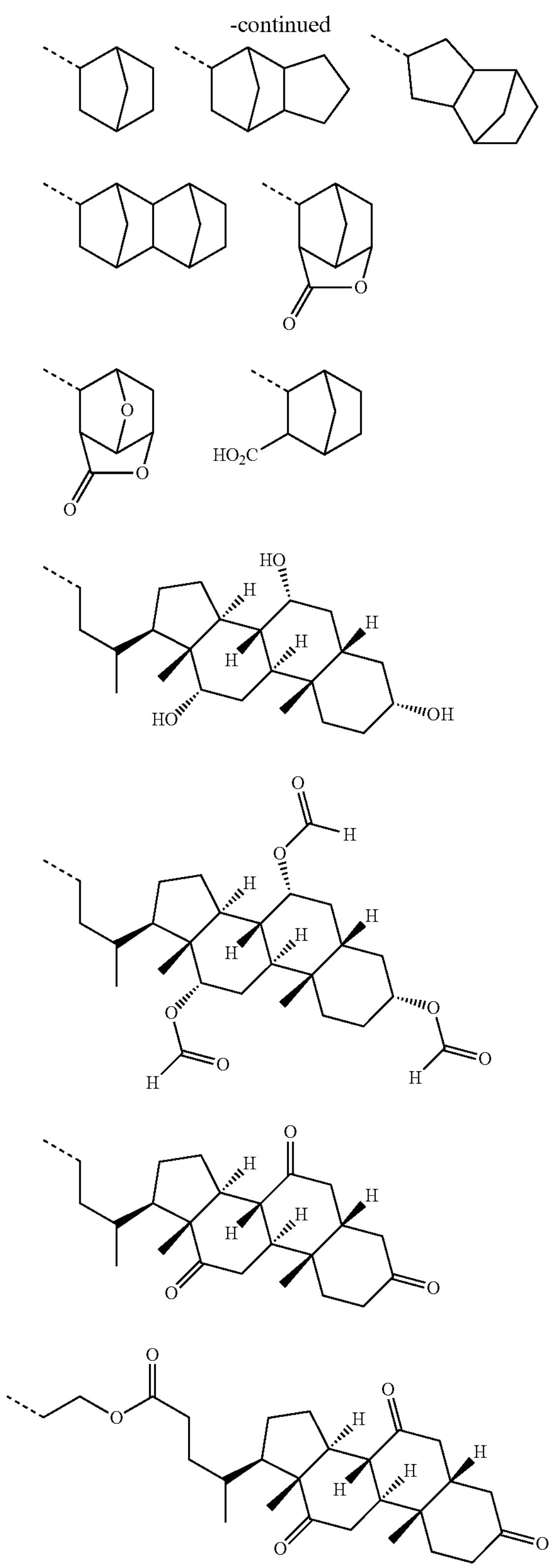

The synthesis of the sulfonium cation in formula (1a) is well known. It may be synthesized by reacting 1-naphthol with tetramethylene sulfoxide in methanol in the presence of hydrogen chloride gas. The synthesis of the sulfonium cation in formula (1b) is also well known. For example, a sulfonium cation in formula (1b) wherein n'=1 may be synthesized by reacting 2-methoxyethyl chloride with 1-naphthol under basic conditions to form 1-(2-methoxyethoxy)naphthalene, then reacting 1-(2-methoxyethoxy)naphthalene with tetramethylene sulfoxide in diphosphorus pentoxide/methanesulfonic acid solution. Also a sulfonium cation in formula (1b) wherein n'=2, 3 or 4 may be similarly synthesized using a corresponding substituted alkyl halide.

The anion of the sulfonium salt having formula (1a) or (1b) may be synthesized according to the teachings of JP-A 2007-145797 and JP-A 2008-299069.

The ion exchange reaction between the cation and the anion may be conducted in an organic solvent such as dichloromethane, ethyl acetate, methyl isobutyl ketone, methanol, ethanol, or acetonitrile, alone or in admixture with water.

In the chemically amplified resist composition, the PAG (D) may be added in any desired amount as long as the objects of the invention are not compromised. An appropriate amount of the PAG is 0.1 to 40 parts, preferably 0.1 to 25 parts by weight per 100 parts by weight of the base resin in the composition. Too high a proportion of the PAG may give rise to problems of degraded resolution and foreign matter upon development and resist film peeling. The PAG may be used alone or in admixture of two or more. The transmittance of the resist film can be controlled by using a PAG having a low transmittance at the exposure wavelength and adjusting the amount of the PAG added.

In the resist composition, any of surfactants commonly used for improving coating characteristics may be added as optional component (E). Reference may be made to component (E) in JP-A 2009-269953. Suitable surfactants are also described in JP-A 2008-122932, JP-A 2010-134012, JP-A 2010-107695, JP-A 2009-191151, and JP-A 2009-98638. There may be used either ordinary surfactants or alkali soluble surfactants. An appropriate amount of the polymeric surfactant added is 0.001 to 20 parts, and more preferably 0.01 to 10 parts by weight per 100 parts by weight of the base resin in the resist composition. Reference should be made to JP-A 2007-297590.

One or more nitrogen-containing organic compounds other than the nitrogen-containing organic compounds defined herein may be added as optional component (F). Reference may be made to JP-A 2009-269953. The nitrogen-containing organic compound (F) may be added in any desired amount as long as the objects of the invention are not compromised. An appropriate amount of the nitrogen-containing organic compound (F) is 0 to 12 parts, preferably 0.001 to 12 parts, and more preferably 0.01 to 8 parts by weight per 100 parts by weight of the base resin in the composition. An excessive amount of the nitrogen-containing organic compound (F) may lead to degraded resolution and pattern difference between dark and bright areas.

The organic acid derivative and/or fluorinated alcohol as component (G) and the dissolution inhibitor having a Mw of up to 3,000 as component (H) are optional. With respect to these compounds, reference may be made to JP-A 2009-269953.

Process

Any well-known lithography may be used to form a resist pattern from the chemically amplified resist composition of the invention. The composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, MoSi, etc.) by a suitable coating technique, typically spin coating. The coating is prebaked on a hot plate at a temperature of 60 to 150° C. for 1 to 10 minutes, preferably 80 to 140° C. for 1 to 5 minutes. The resulting resist film is generally 0.05 to 2.0 μm thick. While a photomask having a desired pattern is placed over the resist film, the resist film is exposed to high-energy radiation such as deep-UV, excimer laser or x-ray. The exposure dose is preferably in the range of 1 to 200 $mJ/cm^2$, more preferably 10 to 100 $mJ/cm^2$. Alternatively, pattern formation may be performed by writing with an electron beam directly (not through a mask). Light exposure may be done by a conventional exposure process or in some cases, by an immersion process of providing liquid impregnation between the mask and the resist. In the case of immersion lithography, a protective film which is insoluble in water may be used. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV or excimer laser having a wavelength of 250 to 190 nm, x-ray, or electron beam. The desired pattern may not be obtainable outside the upper and lower limits of the above range.

The water-insoluble protective coating which is used in the immersion lithography is to prevent the resist film from being leached and to improve water slippage at the film surface and is generally divided into two types. The first type is an organic solvent-strippable protective coating which must be stripped, prior to alkaline development, with an organic solvent in which the resist coating is not dissolvable. The second type is an alkali-soluble protective coating which is soluble in an alkaline developer so that it can be removed simultaneously with the removal of solubilized regions of the resist film. The protective coating of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective coating of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

EXAMPLE

Synthesis Examples, Examples and Comparative Examples are given below for further illustrating the invention, but they are not to be construed as limiting the invention. A weight average molecular weight (Mw) is determined by gel permeation chromatography (GPC) versus polystyrene standards, and a dispersity (Mw/Mn) is computed therefrom.

Synthesis Example 1

Nitrogen-containing organic compounds within the scope of the invention were synthesized by the following procedure.

Synthesis Example 1-1

Synthesis of 1-benzyloxycarbonyl-2-phenylbenzimidazole (Amine-1)

Amine-1

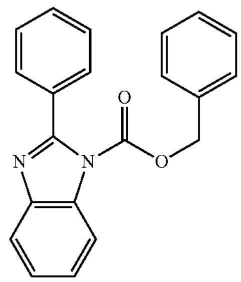

In a nitrogen atmosphere, 107 g of benzyl chlorocarbonate was added dropwise to a solution of 97 g of 2-phenylbenzimidazole and 107 g of 2,6-lutidine in 700 g of tetrahydrofuran, which was heated and stirred at 50° C. for 20 hours. After ordinary aqueous work-up, the insoluble was filtered off. The filtrate was concentrated, washed with hexane, and dried, obtaining 118 g of 1-benzyloxycarbonyl-2-phenylbenzimidazole (yield 72%).

IR (D-ATR): ν=3086, 3066, 3056, 3043, 1746, 1709, 1602, 1534, 1497, 1488, 1470, 1453, 1445, 1388, 1353, 1338, 1314, 1294, 1263, 1213, 1199, 1144, 1081, 1062, 1028, 1018, 990, 957, 937, 908, 879, 856, 840, 793, 765, 758, 750, 742, 712, 697, 687, 635, 615 $cm^{-1}$ $^1$H-NMR (600 MHz in DMSO-$d_6$): δ=5.36 (2H, s), 7.20-7.27 (2H, m), 7.30-7.35 (3H, m), 7.37-7.45 (4H, m), 7.48 (1H, m), 7.65-7.73 (2H, m), 7.76 (1H, m), 7.97 (1H, m) ppm

Synthesis Example 1-2

Synthesis of 1-benzyloxycarbonyl-2-methylbenzimidazole (Amine-2)

Amine-2

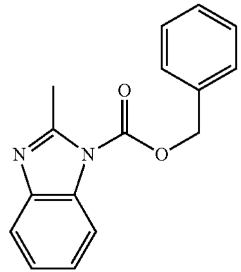

The same procedure as Synthesis Example 1-1 was repeated except that 2-methylbenzimidazole was used instead of 2-phenylbenzimidazole, obtaining 1-benzyloxycarbonyl-2-methylbenzimidazole (yield 70%).

IR (D-ATR): ν=3288, 3030, 1739, 1679, 1605, 1548, 1498, 1471, 1454, 1385, 1330, 1287, 1258, 1211, 1188, 1120, 1087, 1059, 1015, 965, 943, 908, 877, 791, 751, 697, 679 $cm^{-1}$ $^{1}H$-NMR (600 MHz in DMSO-$d_6$): δ=2.70 (3H, s), 5.51 (2H, s), 7.28-7.30 (2H, m), 7.39 (1H, m), 7.43-7.45 (2H, m), 7.56-7.57 (2H, m), 7.60 (1H, m), 7.85 (1H, m) ppm Synthesis Example 1-3-1

Synthesis of 2-cyclohexylbenzimidazole

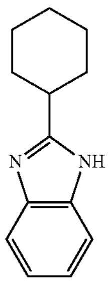 [SMILES: c1ccc2[nH]c(C3CCCCC3)nc2c1]

A mixture of 7 g of o-phenylenediamine and 12.5 g of cyclohexanecarboxylic acid was melted by heating at 130-150° C. and stirred for 8 hours. The solid after reaction was transferred into 130 g of 1 wt % sodium hydroxide aqueous solution to form a suspension, which was filtered and washed with hot water. The crude crystals thus obtained were recrystallized from methanol/water, filtered, and dried, obtaining 8.9 g of 2-cyclohexylimidazole (yield 69%).

Synthesis Example 1-3-2

Synthesis of 1-benzyloxycarbonyl-2-cyclohexylbenzimidazole (Amine-6)

Amine-6

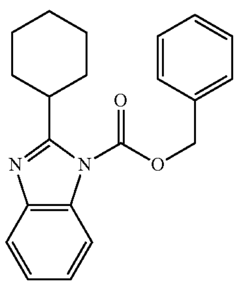

The same procedure as Synthesis Example 1-1 was followed aside from using 2-cyclohexylimidazole synthesized in Synthesis Example 1-3-1. There was obtained 1-benzyloxycarbonyl-2-cyclohexylbenzimidazole (yield 83%).

IR (D-ATR): V=3065, 3037, 2930, 2856, 1742, 1536, 1499, 1473, 1454, 1433, 1390, 1350, 1334, 1315, 1295, 1267, 1249, 1229, 1217, 1191, 1120, 1086, 1019, 967, 910, 894, 872, 846, 794, 765, 752, 739, 697, 648, 637, 580 $cm^{-1}$ $^{1}H$-NMR (300 MHz in DMSO-$d_6$): δ=1.29-2.09 (10H, m), 3.51 (1H, m), 5.50 (2H, s), 7.22-7.33 (2H, m), 7.39-7.53 (5H, m), 7.70 (1H, m), 7.88 (1H, m) ppm Synthesis Example 2

Polymers for use in resist compositions were synthesized according to the following formulation.

Synthesis Example 2-1

Synthesis of Polymer 1

A flask in nitrogen blanket was charged with 50.6 g of 1-(1-methylethyl)cyclopentyl methacrylate, 23.1 g of 2-oxo-4-oxahexahydro-3,5-methano-2H-cyclopenta[b]furan-6-yl methacrylate, 26.3 g of 2-oxotetrahydrofuran-3-yl methacrylate, 1.19 g of dimethyl 2,2'-azobis(2-methyl-propionate) (V601, Wako Pure Chemical Industries, Ltd.), 1.51 g of 2-mercaptoethanol, and 175 g of propylene glycol methyl ether acetate (PMA) to form a monomer/initiator solution. Another flask in nitrogen blanket was charged with 58.3 g of PMA and heated at 80° C. with stirring, to which the monomer/initiator solution was added dropwise over 4 hours. After the completion of dropwise addition, the reaction solution was stirred for 2 hours for polymerization while maintaining the temperature of 80° C., and then cooled to room temperature. With vigorous stirring, the polymerization solution was added dropwise to 1,600 g of methanol whereupon a copolymer precipitate was collected by filtration. The copolymer was washed twice with 600 g of methanol. On vacuum drying at 50° C. for 20 hours, 83.3 g of the copolymer was obtained in white powder form. The copolymer was analyzed by $^{13}C$-NMR, finding a copolymer compositional ratio of 46.4/22.2/31.4 mol % in the described order of monomers. On GPC analysis, the copolymer had a Mw of 6,100.

Polymer-1

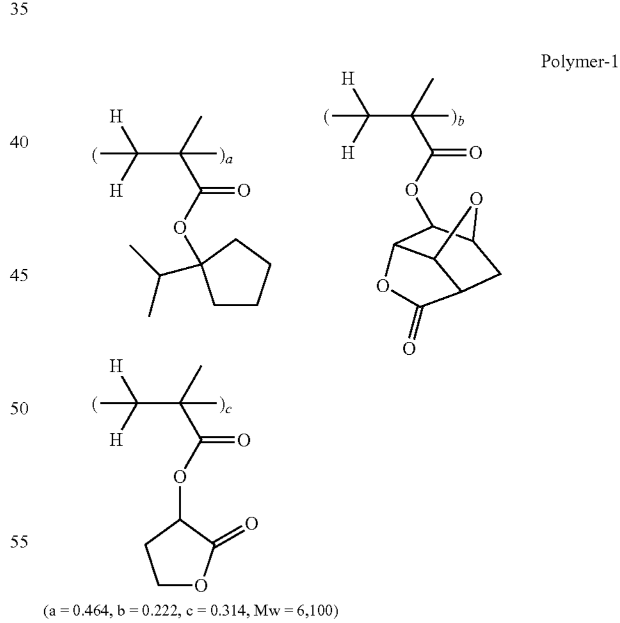

(a = 0.464, b = 0.222, c = 0.314, Mw = 6,100)

Synthesis Example 2-2, 2-3

Synthesis of Polymers 2 and 3

Polymers were prepared by the same procedure as Synthesis Example 2-1 except that the type and amount of monomers used were changed.

Polymer-2

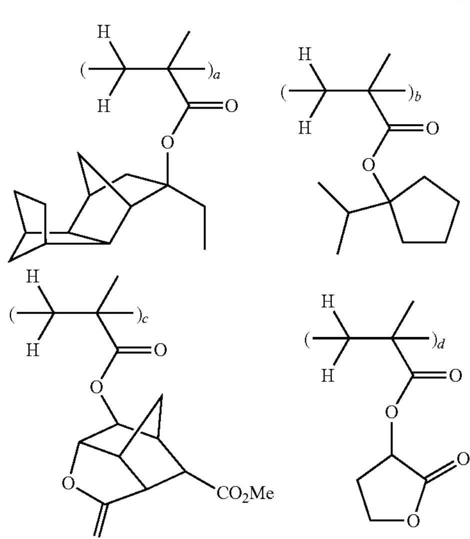

(a = 0.097, b = 0.368, c = 0.318, d = 0.217, Mw = 6,900)

Polymer-3

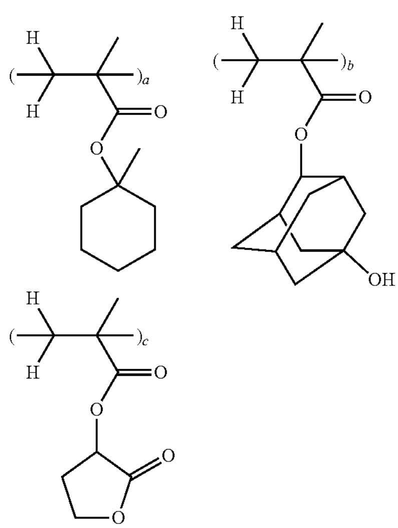

(a = 0.473, b = 0.118, c = 0.409, Mw = 9,800)

Reference Synthesis Example 1

Synthesis of 4-hydroxynaphthyl-1-tetrahydrothiophenium chloride

In 50 g of methanol were dissolved 10 g (0.069 mol) of 1-naphthol and 7.2 g (0.069 mol) of tetramethylene sulfoxide. The solution was cooled to −16° C. An excess of hydrogen chloride gas was fed to the solution at a temperature below 20° C. Nitrogen gas was bubbled to expel the excess of hydrogen chloride. The reaction solution was concentrated and combined with water and diisopropyl ether, from which a water layer was separated. It was an aqueous solution of 4-hydroxynaphthyl-1-tetrahydrothiophenium chloride. This aqueous solution was used in the subsequent step without further isolation.

Reference Synthesis Example 2

Synthesis of 4-hydroxynaphthyl-1-tetrahydrothiophenium 2-(adamantane-1-carbonyloxy)-1,1,3,3,3-pentafluoropropanesulfonate (PAG-1)

An aqueous solution of sodium 1,1,3,3,3-pentafluoro-2-(adamantane-1-carbonyloxy)propanesulfonate (corresponding to 0.021 mol) synthesized according to the formulation described in JP-A 2007-145797 was mixed with the aqueous solution of 4-hydroxynaphthyl-1-tetrahydrothiophenium chloride (corresponding to 0.023 mol) synthesized in Reference Synthesis Example 1. The mixture was extracted with 100 g of dichloromethane and 50 g of methyl isobutyl ketone. The organic layer was washed with water, and the solvent was distilled off in vacuum. The residue was poured into isopropyl ether for crystallization, filtered and dried, obtaining the target compound. White crystal, 6.2 g, yield 43%.

The target compound was analyzed by spectroscopy. The data of infrared (IR) absorption spectroscopy are shown below. In $^{1}$H-NMR analysis, minute amounts of residual solvents (diisopropyl ether, methyl isobutyl ketone) were observed. In $^{19}$F-NMR analysis, trace impurities were observed. The product was the target compound with hydrogen fluoride eliminated from its anion, as described in JP-A 2007-145797.

IR spectra (KBr, $cm^{-1}$) 3133, 2933, 2908, 2855, 1755, 1572, 1370, 1352, 1269, 1213, 1184, 1168, 1103, 1088, 1075, 990, 760, 641

Reference Synthesis Example 3

Synthesis of 1-(2-methoxyethoxy)naphthalene

In 100 g of ethanol were dissolved 50.0 g (0.0347 mol) of 1-naphthol, 34.4 g (0.0364 mol) of 2-methoxyethyl chloride, 14.6 g (0.0365 mol) of sodium hydroxide, and 2.6 g (0.017 mol) of sodium iodide. The solution was heated and stirred at 80° C. for 8 hours. After cooling, the solution was combined with 100 g of water and 200 g of toluene, from which an organic layer was separated. It was washed 5 times with 100 g of 5 wt % sodium hydroxide aqueous solution and then 4 times with 100 g of water. The organic layer was concentrated, obtaining 45 g of oily matter. On vacuum distillation (110° C./13 Pa), 41 g of the target compound was recovered (yield 58%).

Reference Synthesis Example 4

Synthesis of 4-(2-methoxyethoxy)naphthalene-1-tetrahydrothiophenium 2-(adamantane-1-carbonyloxy)-1,1,3,3,3-pentafluoropropanesulfonate (PAG-2)

In 10 g of Eaton's reagent (Aldrich, diphosphorus pentoxide/methanesulfonic acid solution) was dispersed 5.0 g (0.024 mol) of 1-(2-methoxyethoxy)naphthalene in Reference Synthesis Example 3. With stirring, 5.1 g (0.049 mol) of tetramethylene sulfoxide was added dropwise to the dispersion. The solution was matured overnight at room temperature and combined with 30 g of water and 30 g of diisopropyl ether, from which a water layer was separated. The water layer was again washed with 30 g of diisopropyl ether. This aqueous solution was combined with an aqueous solution of sodium 1,1,3,3,3-pentafluoro-2-(adamantane-1-carbonyloxy)propanesulfonate (corresponding to 0.007 mol) synthesized according to the formulation described in JP-A 2007-145797, after which extraction was effected twice with 50 g of dichloromethane. The organic layer was washed with water, and the solvent was distilled off in vacuum. The residue was poured into isopropyl ether for crystallization, filtered and dried, obtaining the target compound. White crystal, 7.9 g, yield 94%.

The target compound was analyzed by spectroscopy. The data of IR absorption spectroscopy are shown below. In $^{1}$H-NMR analysis, a minute amount of residual solvent (diisopropyl ether) was observed.

IR spectra (KBr, $cm^{-1}$) 1744, 1452, 1375, 1337, 1314, 1263, 1212, 1199, 1062, 961, 942, 767, 742, 692

Examples 1 to 11 and Comparative Examples 1 to 6

Resist solutions were prepared by dissolving a polymer, a quencher, and PAG in a solvent mixture containing 0.01 wt % of surfactant A in accordance with the recipe shown in Table 1, and filtering through a Teflon® filter having a pore size of 0.2 μm.

The quencher used was selected from the nitrogen-containing organic compounds (Amine-1, 2, 6) obtained in Synthesis Examples. Other components in Table 1 including the polymer, PAG, solvents, quenchers in Comparative Examples and surfactant are shown below.

P-1: Polymer 1

P-1: Polymer 2

P-3: Polymer 3

Photoacid generators:

PAG-1, PAG-2, and PAG-3 of the following formulae

PAG-1

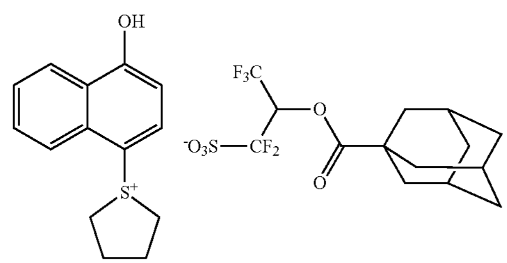

PAG-2

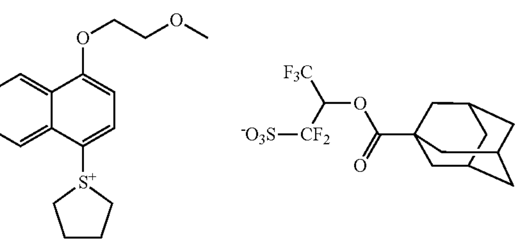

PAG-3

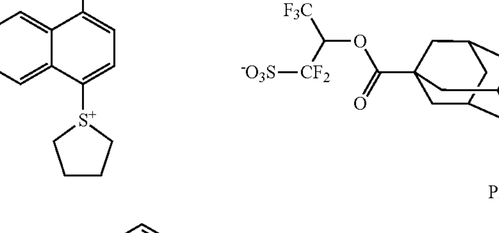

Quenchers: Amine-3, Amine-4, and Amine-5 of the following formulae

Amine-3

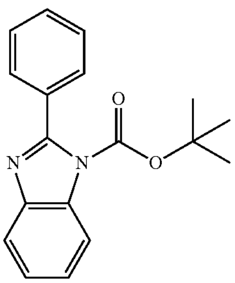

Amine-4

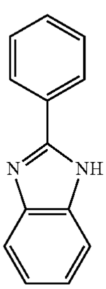

Amine-5

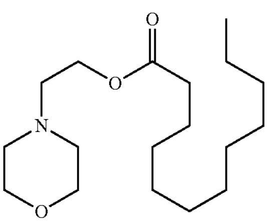

PGMEA: propylene glycol monomethyl ether acetate

GBL: γ-butyrolactone

Alkali-soluble surfactant SF-1: of the formula below (described in JP-A 2008-122932), poly(3,3,3-trifluoro-2-hydroxy-1,1-dimethyl-2-trifluoromethylpropyl methacrylate/1,1,1-trifluoro-2-hydroxy-6-methyl-2-trifluoromethylhept-4-yl methacrylate)

SF-1

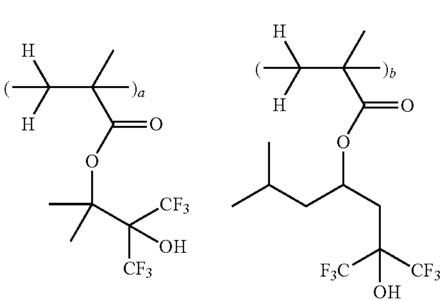

(a = 0.5, b = 0.5, Mw = 7,300)

Surfactant A: 3-methyl-3-(2,2,2-trifluoroethoxymethyl)oxetane/tetrahydrofuran/2,2-dimethyl-1,3-propanediol copolymer (available from Omnova Solutions, Inc.) with the structural formula shown below

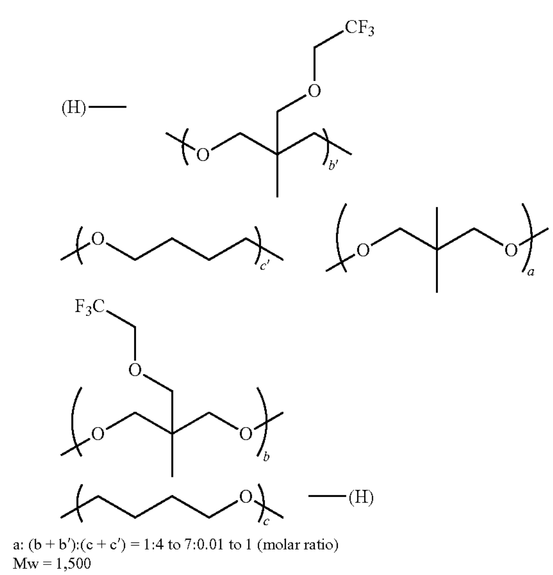

TABLE 1

| | | Resist composition | Resin (pbw) | PAG (pbw) | Quencher (pbw) | Alkali soluble surfactant (pbw) | Solvent 1 (pbw) | Solvent 2 (pbw) |
|---|---|---|---|---|---|---|---|---|
| Example | 1 | R-01 | P-1 (80) | PAG-1 (12) | Amine-1 (4.0) | SF-1 (5.0) | PGMEA (2,700) | GBL (300) |
| | 2 | R-02 | P-1 (80) | PAG-2 (13.1) | Amine-1 (4.0) | SF-1 (5.0) | PGMEA (2,700) | GBL (300) |
| | 3 | R-03 | P-1 (80) | PAG-3 (12.6) | Amine-1 (4.0) | SF-1 (5.0) | PGMEA (2,700) | GBL (300) |
| | 4 | R-04 | P-2 (80) | PAG-1 (12) | Amine-1 (4.0) | SF-1 (5.0) | PGMEA (2,700) | GBL (300) |
| | 5 | R-05 | P-2 (80) | PAG-2 (13.1) | Amine-1 (4.0) | SF-1 (5.0) | PGMEA (2,700) | GBL (300) |
| | 6 | R-06 | P-2 (80) | PAG-3 (12.6) | Amine-1 (4.0) | SF-1 (5.0) | PGMEA (2,700) | GBL (300) |
| | 7 | R-07 | P-3 (80) | PAG-1 (12) | Amine-1 (4.0) | SF-1 (5.0) | PGMEA (2,700) | GBL (300) |
| | 8 | R-08 | P-3 (80) | PAG-2 (13.1) | Amine-1 (4.0) | SF-1 (5.0) | PGMEA (2,700) | GBL (300) |
| | 9 | R-09 | P-3 (80) | PAG-3 (12.6) | Amine-1 (4.0) | SF-1 (5.0) | PGMEA (2,700) | GBL (300) |
| | 10 | R-10 | P-3 (80) | PAG-1 (12) | Amine-2 (3.3) | SF-1 (5.0) | PGMEA (2,700) | GBL (300) |
| | 11 | R-11 | P-1 (80) | PAG-1 (12) | Amine-6 (4.1) | SF-1 (5.0) | PGMEA (2,700) | GBL (300) |
| Comparative Example | 1 | R-12 | P-1 (80) | PAG-1 (12) | Amine-3 (3.6) | SF-1 (5.0) | PGMEA (2,700) | GBL (300) |
| | 2 | R-13 | P-1 (80) | PAG-3 (12.6) | Amine-3 (3.6) | SF-1 (5.0) | PGMEA (2,700) | GBL (300) |
| | 3 | R-14 | P-1 (80) | PAG-1 (12) | Amine-4 (2.4) | SF-1 (5.0) | PGMEA (2,700) | GBL (300) |
| | 4 | R-15 | P-1 (80) | PAG-3 (12.6) | Amine-4 (2.4) | SF-1 (5.0) | PGMEA (2,700) | GBL (300) |
| | 5 | R-16 | P-1 (80) | PAG-1 (12) | Amine-5 (3.8) | SF-1 (5.0) | PGMEA (2,700) | GBL (300) |
| | 6 | R-17 | P-1 (80) | PAG-3 (12.6) | Amine-5 (3.8) | SF-1 (5.0) | PGMEA (2,700) | GBL (300) |

Evaluation of Storage Stability and Dark-Bright Difference of Resist Composition on ArF Lithography An antireflective coating liquid ARC-29A (Nissan Chemical Co., Ltd.) was coated onto a silicon substrate and baked at 200° C. for 60 seconds to form an antireflective coating of 100 nm thick. The resist solution, prepared above, was spin coated onto the ARC and baked on a hot plate at 100° C. for 60 seconds to form a resist film of 120 nm thick. The resist film was exposed by the ArF immersion lithography on an ArF excimer laser scanner model NSR-S601C (Nikon Corp., NA 1.30, dipole illumination, Cr mask), post-exposure baked (PEB) at 80° C. for 60 seconds, and developed with a 2.38 wt % aqueous solution of tetramethylammonium hydroxide (TMAH) for 60 seconds.

An optimum exposure dose (Eop, mJ/cm$^2$) was the exposure which provided a 1:1 resolution at the top and bottom of a 40-nm grouped line-and-space pattern. This evaluation used the line-and-space pattern in a dark area (opposed sides of a 10-line L/S pattern were light-shielded by bulk patterns). The pattern profiles in the dark area and a bright area (a 10-line L/S pattern was flanked with broad spaces, i.e., transmissive area), both printed in the optimum dose (Eop), were observed under electron microscope.

The pattern profile in the dark area was evaluated according to the following criteria.

Rectangular: perpendicular line sidewalls, little size changes from bottom (near substrate) to top, acceptable T-top: size enlargement near line top, unacceptable Top rounding: rounding and size reduction near line top, unacceptable Also the line width of a L/S pattern in the bright area printed in the optimum dose (Eop) was measured and reported as Dark/Bright bias. A smaller value indicates a smaller size difference between the dark and bright areas, which is better.

The storage stability of resist solution was evaluated by comparing an initial Eop of a freshly prepared resist solution with an aged Eop of a resist solution which was aged for one month at 20° C. after preparation. A sensitivity change was calculated by the equation:

Sensitivity change(%)=[(aged Eop−initial Eop)/(initial Eop)]×100

A negative value indicates that the resist increased its sensitivity. A smaller absolute value means a less change with time of the resist composition, indicating a higher storage stability.

The evaluation results of the resist compositions are tabulated in Table 2.

TABLE 2

| | | Resist composition | Optimum dose (mJ/cm$^2$) | Pattern profile in dark area | Dark/Bright bias (nm) | Sensitivity change (%) |
|---|---|---|---|---|---|---|
| Example | 1 | R-01 | 50 | rectangular | 1 | 0 |
| | 2 | R-02 | 39 | rectangular | 1 | 0 |
| | 3 | R-03 | 20 | rectangular | 0 | 0 |
| | 4 | R-04 | 46 | rectangular | 0 | 0 |
| | 5 | R-05 | 33 | rectangular | 1 | 0 |
| | 6 | R-06 | 18 | rectangular | 0 | 0 |
| | 7 | R-07 | 62 | rectangular | 2 | 0 |
| | 8 | R-08 | 50 | rectangular | 1 | 0 |
| | 9 | R-09 | 25 | rectangular | 1 | 0 |
| | 10 | R-10 | 48 | rectangular | 1 | 0 |
| | 11 | R-11 | 50 | rectangular | 1 | 0 |
| Comparative Example | 1 | R-12 | 51 | top rounding | 2 | 0 |
| | 2 | R-13 | 20 | top rounding | 1 | 0 |
| | 3 | R-14 | 49 | T-top | 7 | −6 |
| | 4 | R-15 | 19 | T-top | 8 | 0 |
| | 5 | R-16 | 55 | T-top | 13 | −9 |
| | 6 | R-17 | 24 | T-top | 10 | 0 |

A comparison of Examples with Comparative Examples in Table 2 reveals that resist compositions comprising the nitrogen-containing organic compounds defined herein as the quencher offer a better pattern profile in the dark area and a smaller size difference between dark and bright areas. Also, a comparison of Example 1 with Comparative Example 3 or 5 indicates that the resist composition comprising the nitrogen-containing organic compound defined herein as the quencher does not undergo a sensitivity change during shelf storage nor detract from the activity of the alkylsulfonium salt PAG.

It is demonstrated that the resist composition comprising the nitrogen-containing organic compound defined herein as the quencher is improved in resolution, forms a pattern of rectangular profile and minimized dark-bright difference, and compensates for the loss of storage stability of alkylsulfonium PAG.

Japanese Patent Application No. 2010-189289 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A chemically amplified positive resist composition comprising:

(A) a nitrogen-containing organic compound having the general formula (3):

(3)

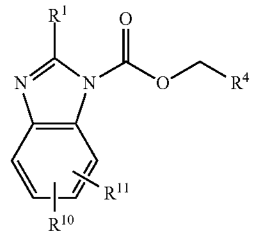

wherein $R^1$ is hydrogen, a straight, branched or cyclic $C_1$-$C_{15}$ alkyl group, or $C_6$-$C_{15}$ aryl group, $R^4$ is an optionally alkoxy-substituted $C_6$-$C_{15}$ aryl group, and $R^{10}$ and $R^{11}$ are each independently hydrogen or $C_1$-$C_6$ alkyl, as a quencher, (B) an organic solvent, (C) a base resin which changes its solubility in alkaline developer under the action of an acid, and (D) a photoacid generator.

2. The chemically amplified positive resist composition of claim 1 wherein the photoacid generator (D) is a sulfonium salt having the general formula (2):

(2)

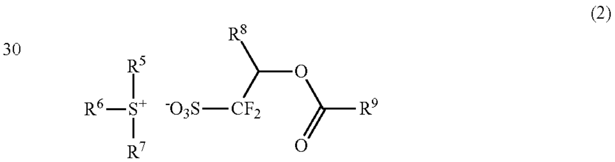

wherein $R^5$, $R^6$, and $R^7$ are each independently a straight or branched alkyl, alkenyl or oxoalkenyl group of 1 to 10 carbon atoms which may contain fluorine, hydroxyl or ether bond, or a substituted or unsubstituted aryl, aralkyl or aryloxoalkyl group of 6 to 18 carbon atoms, or two or more of $R^5$, $R^6$, and $R^7$ may bond together to form a ring with the sulfur atom to which they are attached, $R^8$ is hydrogen or trifluoromethyl, and $R^9$ is a monovalent, straight, branched or cyclic $C_6$-$C_{30}$ hydrocarbon group which may contain a heteroatom.

3. A process for forming a pattern, comprising the steps of coating the resist composition of claim 1 onto a substrate, heat treating the composition to form a resist film, exposing the resist film to high-energy radiation through a photomask, optionally heat treating, and developing the exposed resist film with a developer.

4. A process for forming a pattern, comprising the steps of coating the resist composition of claim 1 onto a substrate, heat treating the composition to form a resist film, coating a protective film onto the resist film, exposing the resist film to high-energy radiation through a photomask with water held between the substrate and a projection lens, optionally heat treating, and developing the exposed resist film with a developer.

* * * * *